US011154675B2

(12) United States Patent
Buschke et al.

(10) Patent No.: US 11,154,675 B2
(45) Date of Patent: Oct. 26, 2021

(54) ANESTHESIA VENTILATOR FOR AUTOMATIC VENTILATION AS WELL AS FOR THE DETECTION OF AN OPERATING STATE CONCERNING THE AUTOMATIC VENTILATION

(71) Applicant: Drägerwerk AG & Co. KGaA, Lübeck (DE)

(72) Inventors: Wilfried Buschke, Lübeck (DE); Christoph Hörmann, Mank (AT); Stefan Mersmann, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 436 days.

(21) Appl. No.: 15/780,459

(22) PCT Filed: Nov. 21, 2016

(86) PCT No.: PCT/EP2016/001951
§ 371 (c)(1),
(2) Date: May 31, 2018

(87) PCT Pub. No.: WO2017/092850
PCT Pub. Date: Jun. 8, 2017

(65) Prior Publication Data
US 2018/0353717 A1    Dec. 13, 2018

(30) Foreign Application Priority Data

Dec. 2, 2015    (DE) .................. 10 2015 015 441.9

(51) Int. Cl.
*A61M 16/00* (2006.01)
*A61M 16/01* (2006.01)
(Continued)

(52) U.S. Cl.
CPC ...... *A61M 16/024* (2017.08); *A61M 16/0003* (2014.02); *A61M 16/0051* (2013.01);
(Continued)

(58) Field of Classification Search
CPC ............ A61M 16/024; A61M 16/0891; A61M 16/104; A61M 16/0003; A61M 16/01;
(Continued)

(56) References Cited

U.S. PATENT DOCUMENTS 4,838,257 A * 6/1989 Hatch .................. A61M 16/204
128/204.18
5,237,990 A * 8/1993 Psaros .................... A61M 16/18
128/203.12
(Continued)

FOREIGN PATENT DOCUMENTS

| CN | 1622839 A | 6/2005 |
| CN | 101318046 A | 12/2008 |

(Continued)

OTHER PUBLICATIONS

"Modes of Ventilation in Intensive Care," Karin Deden, Dräger Medical GmbH. The reference is discussed on p. 16 of Applicant's substitute specification.

(Continued)

*Primary Examiner* — Rachel T Sippel
*Assistant Examiner* — Kelsey E Baller
(74) *Attorney, Agent, or Firm* — McGlew and Tuttle, P.C.

(57) ABSTRACT

An anesthesia ventilator, for the automated ventilation of a patient, includes an expiratory port and an inspiratory port for connecting a patient ventilation tube for a breathing gas, a breathing gas delivery unit, a breathing gas volume flow sensor, a breathing gas sensor for detecting a carbon dioxide concentration, a pressure sensor for detecting a pressure of the breathing gas, and a computer. The computer is config-
(Continued)

ured to actuate the breathing gas delivery unit in a first mode of operation as a function of a preset ventilation rate, of the detected pressure and of a preset desired pressure value. The computer is configured to detect the presence of a desired operating state concerning the automated ventilation on the basis of the detected volume flow and of the detected carbon dioxide concentration and to make possible a transition to a second mode of operation in case of detection.

13 Claims, 13 Drawing Sheets

(51) Int. Cl.
*A61M 16/08* (2006.01)
*A61M 16/10* (2006.01)
*A61M 16/18* (2006.01)
*A61M 16/22* (2006.01)
A61M 16/20 (2006.01)

(52) U.S. Cl.
CPC ........ *A61M 16/01* (2013.01); *A61M 16/0891* (2014.02); *A61M 16/104* (2013.01); *A61M 16/18* (2013.01); *A61M 16/0072* (2013.01); *A61M 16/085* (2014.02); *A61M 16/208* (2013.01); *A61M 16/22* (2013.01); *A61M 2016/0027* (2013.01); *A61M 2016/0033* (2013.01); *A61M 2016/0039* (2013.01); *A61M 2205/50* (2013.01); *A61M 2230/432* (2013.01); *A61M 2230/437* (2013.01)

(58) Field of Classification Search
CPC .... A61M 16/22; A61M 16/00; A61M 16/021; A61M 16/022; A61M 16/026; A61M 16/10; A61M 16/18; A61M 16/0087; A61M 16/009; A61M 2016/0027; A61M 2016/103; A61M 2016/0015; A61M 2016/0018; A61M 2016/003; A61M 2016/0033; A61M 2016/0036; A61M 2016/0039; A61M 2016/0042; A61M 2202/3334; A61M 2202/3351; A61M 2202/3355; A61M 2202/0241; A61M 2202/0225; A61M 2202/0021; A61M 2202/0007
See application file for complete search history.

(56) References Cited

U.S. PATENT DOCUMENTS

| | | | |
|---|---|---|---|
| 5,752,509 A | 5/1998 | Burkhard et al. | |
| 6,123,072 A * | 9/2000 | Downs ................. | A61M 16/00 128/204.21 |
| 6,125,848 A * | 10/2000 | Hendrickson ......... | A61M 16/08 128/204.22 |
| 6,216,690 B1 * | 4/2001 | Keitel ................... | A61M 16/18 128/203.12 |
| 2008/0041381 A1* | 2/2008 | Tham ................ | A61M 16/0051 128/204.23 |
| 2010/0241064 A1 | 9/2010 | Puri | |
| 2015/0059744 A1* | 3/2015 | Fisher ................... | A61B 5/087 128/203.14 |
| 2015/0231351 A1* | 8/2015 | Jonson .................. | A61B 5/087 128/204.22 |
| 2015/0374947 A1* | 12/2015 | Wallen ................ | A61M 16/024 128/202.22 |
| 2016/0310690 A1* | 10/2016 | Summers ............. | A61M 39/26 |
| 2016/0345863 A1* | 12/2016 | Johnson ............. | A61M 16/085 |
| 2018/0214648 A1* | 8/2018 | Heinonen ........... | A61M 16/026 |
| 2020/0038611 A1* | 2/2020 | Isaza ................. | A61M 16/205 |

FOREIGN PATENT DOCUMENTS

| | | |
|---|---|---|
| CN | 101472631 A | 7/2009 |
| DE | 10 2005 012340 B3 | 5/2006 |
| DE | 10 2012 024 672 A1 | 6/2014 |
| DE | 10 2013 002 408 A1 | 8/2014 |
| DE | 10 2015 015 439 A1 | 6/2017 |
| DE | 10 2015 015 440 A1 | 6/2017 |
| EP | 1 974 763 A1 | 10/2008 |
| JP | H0924099 A1 | 1/1997 |
| WO | 2009/050736 A1 | 4/2009 |

OTHER PUBLICATIONS

"Zeus Infinity Empowered" Manual, Dräger Medical AG & Co. KG, 1st edition, Feb. 2009.
"Primus Infinity Empowered," Dräger Medical GmbH, Edition: 3/2010/09, pp. 132-134.

* cited by examiner

| Level of ventilation | | | |
|---|---|---|---|
| normal ventilated | Lung mechanic | | |
| KOZ Parameter | normal | obstructive | restrictive |
| etCO$_2$U1 [mmHg] | 35 | 45 | 35 |
| etCO$_2$O1 [mmHg] | 45 | 45 | 45 |
| Level of ventilation | | | |
| mild hyperventilated | Lung mechanic | | |
| KOZ Parameter | normal | obstructive | restrictive |
| etCO$_2$U1 [mmHg] | 30 | 40 | 30 |
| etCO$_2$O1 [mmHg] | 40 | 50 | 40 |
| | Lung mechanic | | |
| KOZ Parameter | normal | obstructive | restrictive |
| VTU1 [ml/kg] | 7 | 3 | 2 |
| VTO1 [ml/kg] | 10 | 10 | 6 |

T3

| Classification of Ventilation ($V_T$) (CoV_VT) | |
|---|---|
| $V_T$ | $V_T$-Range |
| very low | VT < VTU2 |
| low | VTU2 < VT < VTU1 |
| normal | VTU1 ≤ VT ≤ VTO1 |
| high | VTO2 > VT > VTO1 |
| very high | VT > VTO2 |

T4

| Classification of Ventilation $etCO_2$ (CoV_$etCO_2$) | |
|---|---|
| $etCO_2$ | $etCO_2$.Range |
| severe hyperventilated | $etCO_2$ < $etCO_2$U2 |
| mild hyperventilated | $etCO_2$U2 < $etCO_2$ < $etCO_2$U1 |
| normoventilated | $etCO_2$U1 ≤ $etCO_2$ ≤ $etCO_2$O1 |
| mild hypoventilated | $etCO_2$O2 > $etCO_2$ > $etCO_2$O1 |
| severe hypoventilated | $etCO_2$ > $etCO_2$O2 |

FIG. 12

ANESTHESIA VENTILATOR FOR AUTOMATIC VENTILATION AS WELL AS FOR THE DETECTION OF AN OPERATING STATE CONCERNING THE AUTOMATIC VENTILATION

CROSS REFERENCE TO RELATED APPLICATIONS

This application is a United States National Phase Application of International Application PCT/EP2016/001951, filed Nov. 21, 2016, and claims the benefit of priority under 35 U.S.C. § 119 of German Application 10 2015 015 441.9, filed Dec. 2, 2015, the entire contents of which are incorporated herein by reference.

FIELD OF THE INVENTION

The present invention relates to an anesthesia ventilator (also known as a respirator) for the automated ventilation (also known as respiration) of a patient. The present invention further relates to a process for operating an anesthesia ventilator for the automated ventilation of a patient.

BACKGROUND OF THE INVENTION

Anesthesia ventilators as well as processes in which a pressure control ventilation of a patient is carried out are known from the state of the art.

It is further known that a so-called weaning, in which the patient is maintained in a so-called comfort zone, is carried out within the framework of such ventilation processes, wherein a desired pressure value or a pressure support value is adapted as a function of a detected tidal volume and of an end-expiratory carbon dioxide concentration for the purpose of weaning within the framework of a pressure support ventilation. Such processes are also known as so-called "Smart-Care/PS" processes.

SUMMARY OF THE INVENTION

An object of the present invention is to carry out by means of an anesthesia ventilator a pressure-controlled ventilation of a patient, in which not only does the anesthesia ventilator carry out an automated ventilation of the patient, but in which a changeover between modes of operation is also advantageously possible.

According to the invention, an anesthesia ventilator is provided for the automated ventilation of a patient, having an expiratory port and an inspiratory port for connecting a ventilation tube facing the patient for a breathing gas, a breathing gas delivery unit, at least one volume flow sensor for detecting a volume flow of the breathing gas, at least one breathing gas sensor for detecting a carbon dioxide concentration, as well as at least one pressure sensor for detecting a pressure of the breathing gas and further at least one computer. The computer is configured to actuate the breathing gas delivery unit as a function of a preset ventilation rate, of the detected pressure and of a preset desired pressure value in a first mode of operation. The computer is further configured to detect the presence of a desired operating state concerning the automated ventilation on the basis of the detected volume flow and of the detected carbon dioxide concentration, and to make possible, in case the operating state is detected, a changeover into a second mode of operation, in which the computer actuates the breathing gas delivery unit such that a pressure-controlled ventilation or a pressure support ventilation is carried out.

The device according to the present invention is advantageous because this device can detect on the basis of the detected volume flow as well as of the detected carbon dioxide concentration that a desired operating state of the ventilation is present. Such an operating state is present when a variable derived from the volume flow, preferably a tidal volume, and a variable derived from the carbon dioxide concentration, preferably an end-expiratory carbon dioxide concentration, have respective desired correlations or value constellations to respective preset limit values. It can possibly be derived hereby that a changeover into a second mode of operation of the ventilation is acceptable for the patient.

The computer is preferably configured to make possible the changeover into the second mode of operation if the operating state is detected within a preset time period. It is ensured as a result that there are no further continual attempts or waiting for the operating state to become established, but the process only leads over into the second operating mode if the operating state is reached within a reasonable or preset time period. The computer preferably carries out the changeover into the second mode of operation automatically. An output signal, which indicates the presence of the desired operating state or the changeover into the second mode of operation, is preferably outputted at the time of this automatic changeover as well. A clinician is informed hereby that the operating state is reached and that a change in the mode of operation is taking place.

The computer is preferably configured to output, in case the operating state is detected, an output signal, which indicates the presence of the desired operating state, as well as to change over into the second mode of operation as a function of an input signal. If the operating state is present, this can be an indication for a clinician that the patient possibly has a desired breathing characteristic. The output of the output signal, which indicates the presence of the operating state of the device concerning the automated ventilation, can then be an indication for a clinician to take a changeover from the first mode of operation to a second mode of operation into consideration. The clinician can then bring about a transition into the second mode of operation by means of an input signal. A pressure control ventilation or a pressure support ventilation may then be carried out in the second mode of operation. It is a usual situation within the framework of anesthesia that a patient is ventilated by means of pressure control ventilation. A clinician has at times the task of determining a time at which he would like to ventilate a patient by the ventilator in a very specific mode of operation, preferably in the second mode of operation. Since the clinician must now consider whether the patient is stable enough to be able to be ventilated by means of such a second mode of operation, the clinician must possibly take properties of a breathing activity of the patient into consideration. The indication that the desired operating state is present may be useful for this for the clinician. The device according to the present invention automates this ventilation in a preferably especially advantageous manner, because the device can detect the presence of the operating state concerning the automated ventilation on the basis of the volume flow as well as of the carbon dioxide concentration and it then displays this to the clinician by outputting the output signal. If the clinician decides himself that he would indeed like to change over the device into the other, second mode of operation, he can bring this about in an automated manner under his control by an input or an input signal. Thus, the clinician will ultimately decide whether the second mode of operation will be carried out, but the clinician is supported in his decision by the output of the output signal.

According to an advantageous embodiment the computer is configured to determine a tidal volume fed to the patient in the first mode of operation on the basis of the detected volume flow and further to determine an end-expiratory carbon dioxide concentration on the basis of the detected carbon dioxide concentration as well as further to perform an adaptation of the desired pressure value and an adaptation of the ventilation rate as a function of the determined tidal volume, of an upper volume limit value, of a lower volume limit value, of the determined end-expiratory carbon dioxide concentration, of an upper concentration limit value and of a lower concentration limit value. This embodiment of the device is advantageous because both the desired pressure value and the ventilation rate can be adapted on the basis of the defined limit values as well as of the measured tidal volume as well as of the end-expiratory carbon dioxide concentration in the course of the first operating mode, in which a pressure control ventilation is carried out, in order to make it possible to maintain the tidal volume breathed by the patient as well as the end-expiatory carbon dioxide concentration within limits defined by the limit values, i.e., in a comfort zone. The anesthesia ventilator preferably detects the presence of the desired operating state in the case in which the tidal volume is between the upper and lower volume limit values and, further, the end-expiratory carbon dioxide concentration is between the upper concentration limit value and the lower concentration limit value.

Further, the anesthesia ventilator preferably has at least one breathing gas sensor for detecting an anesthetic gas concentration in the breathing gas, wherein the desired operating state is a first desired operating state, wherein the computer is further configured to detect the presence of a second desired operating state concerning the automated ventilation in the second mode of operation on the basis of the detected anesthetic gas concentration, and to output, in case the second operating state is detected, a second output signal, which indicates the presence of the second desired operating state. This embodiment of the present invention is advantageous because it is thus possible to inform the clinician during the second operating mode that another, second desired operating state has been reached concerning the automated ventilation. The clinician can then possibly take a change in the automated ventilation into consideration. When the second operating state is detected, there preferably is, furthermore, an automatic transition from the second mode of operation to a third mode of operation, in which the computer actuates the delivery unit such that a pressure support ventilation is carried out.

The computer is further preferably configured to detect in the second mode of operation the presence of the second desired operating state concerning the automated ventilation as a function of an information signal, which indicates an operating state of the anesthetic evaporator. This embodiment of the present invention is advantageous because it is thus also possible in the course of checking for the presence of the second operating state to take into consideration whether the anesthetic evaporator as a main source of the anesthetic has a desired operating state. If, for example, the anesthetic evaporator is configured in the desired operating state, the output signal can be interpreted by the clinician as an indication that an end phase of the anesthesia ventilation could have been reached.

The computer is preferably configured to change over, when the second operating state is detected, as a function of an additional input signal, into a third mode of operation, in which the computer actuates the breathing gas delivery unit such that a pressure support ventilation is carried out. This embodiment of the present invention is advantageous because the output signal can be interpreted by the clinician as an indication of the presence of the second operating state to take a changeover into a third mode of operation into consideration, in which the patient undergoes only pressure support ventilation. A pressure support ventilation means that the patient displays spontaneous breathing activity himself, which is desirable precisely until the end of the anesthetic ventilation after stopping the supply of more anesthetic. The clinician himself does not have to now change over to the mode of pressure support ventilation by setting certain parameters, but the computer changes over into such a mode of the pressure support ventilation based on the input by the clinician in an automated manner under the control of the clinician.

The computer is preferably configured to actuate the breathing gas delivery unit in the second mode of operation for a pressure control ventilation or for a pressure support ventilation as a function of the detected pressure and of a second preset desired pressure value, further to determine a tidal volume fed to the patient on the basis of the detected volume flow, to determine an end-expiratory carbon dioxide concentration on the basis of the detected carbon dioxide concentration, as well as further to perform an adaptation of the desired pressure value and an adaptation of a ventilation rate as a function of the determined tidal volume, of an upper volume limit value, of a lower volume limit value, of the determined end-expiratory carbon dioxide concentration, of an upper concentration limit value and of a lower concentration limit value. This embodiment of the present invention is advantageous because the pressure control ventilation or the pressure support ventilation is adapted during the second mode of operation not only concerning the desired pressure value but also concerning a ventilation rate as a function of the tidal volume and also of the end-expiratory carbon dioxide concentration.

The computer is preferably configured to actuate the breathing gas delivery unit as a function of the detected pressure and of a preset desired pressure value in the third mode of operation, wherein the computer is further configured to perform an adaptation of the desired pressure value as a function of the detected anesthesia gas concentration. This embodiment of the present invention is advantageous because the device can thus take the anesthetic gas concentration into consideration in the third mode of operation in order to adapt the desired pressure value in this phase of the pressure support ventilation.

Further, a process for operating an anesthesia ventilator for an automated ventilation of a patient is proposed, comprising the steps: feeding of a breathing gas to a patient via an inspiratory port and returning of the breathing gas via an expiratory port by operating a breathing gas delivery unit; detecting a volume flow of the breathing gas by means of at least one volume flow sensor; detecting a carbon dioxide concentration in the breathing gas by means of at least one breathing gas sensor; detecting a pressure of the breathing gas by means of at least one pressure sensor; as well as, in a first mode of operation, actuating the breathing gas delivery unit as a function of a preset ventilation rate, of the detected pressure and of a preset desired pressure value by means of at least one computer, characterized by the detection of the presence of a desired operating state concerning the automated ventilation on the basis of the detected volume flow and of the detected carbon dioxide concentration and, in case the operating state is detected, by making it possible to change over into a second mode of operation, in which the computer actuates the breathing gas delivery unit such that a pressure control ventilation or a pressure support ventilation is carried out.

The process is preferably characterized in that when the operating state is detected, an output signal is outputted, which output signal indicates the presence of the desired operating state, as well as in that depending on an input signal, there is a changeover into a second mode of operation, in which the breathing gas delivery unit is actuated by means of the computer such that a pressure control ventilation or a pressure support ventilation is carried out.

Further, a computer for an anesthesia ventilator for the automated ventilation of a patient is proposed, which is configured to detect a volume flow signal, which indicates a volume flow of a breathing gas, further to detect a carbon dioxide concentration signal, which indicates a carbon dioxide concentration in the breathing gas, further to detect a pressure signal, which indicates a pressure of the breathing gas, in a first mode of operation. The computer is further configured to provide an actuating signal for a breathing gas delivery unit, wherein the computer determines the actuating signal as a function of a preset ventilation rate, of the detected pressure signal and of a preset desired pressure value, wherein the computer is further configured to detect the presence of a desired operating state concerning the automated ventilation on the basis of the detected volume flow and of the detected carbon dioxide concentration, and, when the operating state is detected, to make possible a changeover into a second mode of operation, in which the computer actuates the breathing gas delivery unit such that a pressure control ventilation or a pressure support ventilation is carried out.

The computer is preferably configured to output, when the operating state is detected, an output signal, which indicates the presence of the desired operating state, as well as to change over, as a function of an input signal, into a second mode of operation, in which the computer actuates the breathing gas delivery unit such that a pressure control ventilation or a pressure support ventilation is carried out.

Further, a process for operating an anesthesia ventilator for the automated ventilation of a patient is proposed, comprising the steps: detection of a volume flow signal, which indicates a volume flow of a breathing gas; detection of a carbon dioxide concentration signal, which indicates a carbon dioxide concentration in the breathing gas; detection of a pressure signal, which indicates a pressure of the breathing gas, in a first mode of operation; provision of an actuating signal for a breathing gas delivery unit, wherein the computer determines the actuating signal as a function of a preset ventilation rate, of the detected pressure signal and of a preset desired pressure value, characterized by the detection of the presence of a desired operating state concerning the automated ventilation on the basis of the detected volume flow and of the detected carbon dioxide concentration and, in case the presence is detected, making it possible to change over into a second mode of operation, in which the computer actuates the breathing gas delivery unit such that a pressure control ventilation or a pressure support ventilation is carried out.

If the presence is detected, an output signal, which indicates the presence of the desired operating state, is preferably outputted, and, depending on an input signal, there is a changeover into a second mode of operation, in which the breathing gas delivery unit is actuated such that a pressure control ventilation or a pressure support ventilation is carried out.

It is further proposed that the above-described process for operating an anesthesia ventilator be provided such that the process is carried out with a computer program on at least one computer.

The present invention will be explained in more detail below on the basis of special embodiments without limitation of the general inventive idea on the basis of the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 12 is a view of respective tables for determining degrees of ventilation and gas exchange rates relative to a tidal volume and to an end-expiratory carbon dioxide concentration.

DESCRIPTION OF THE PREFERRED EMBODIMENTS

Figure 1:
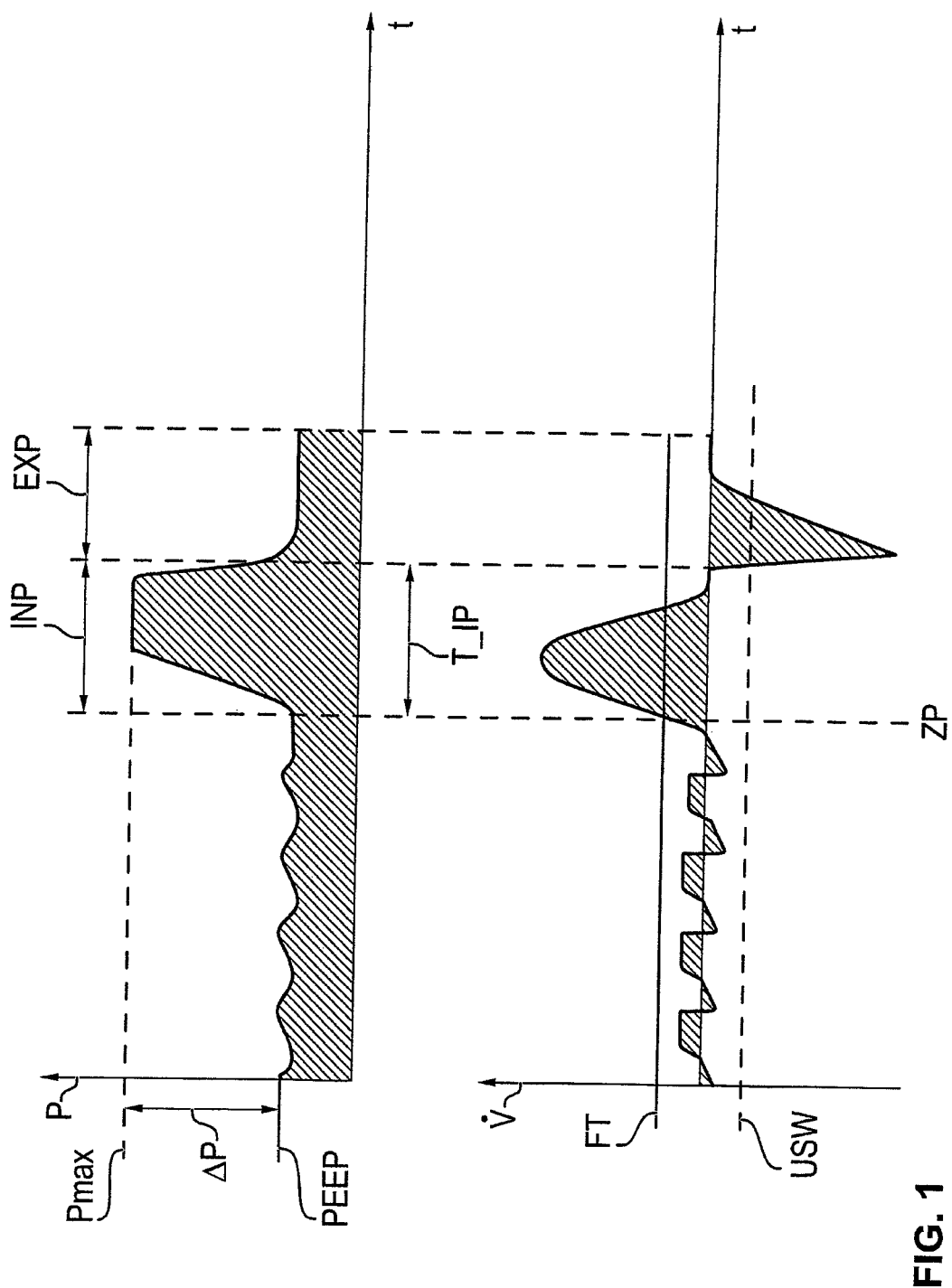
FIG. 1 is a graph view showing a pressure curve over time as well as a volume flow curve over time in the course of an inhalation and an exhalation.

Referring to the drawings, FIGS. 1 through 4 show curves known from the state of the art, on the basis of which the principles of a trigger control, of a pressure support ventilation, of a pressure control ventilation without attempts at spontaneous breathing permitted, as well as of a pressure control ventilation with attempts at spontaneous breathing permitted will now be explained.

FIG. 1 shows a pressure curve P as well as a volume flow curve $\dot{V}$ over the time t. A flow triggering is the fact that a flow threshold value FT is exceeded by the volume flow $\dot{V}$ at a triggering time ZP, so that the pressure will then be controlled by the minimum pressure PEEP (Positive End Expiratory Pressure) to the maximum pressure Pmax by a pressure increase ΔP during the inspiratory phase INP. The expiratory phase EXP follows the inspiratory phase INP. The start of the expiratory phase EXP can preferably be detected by means of a lower threshold value USW, through which the volume flow $\dot{V}$ must pass with a negative signal curve.

Figure 2:
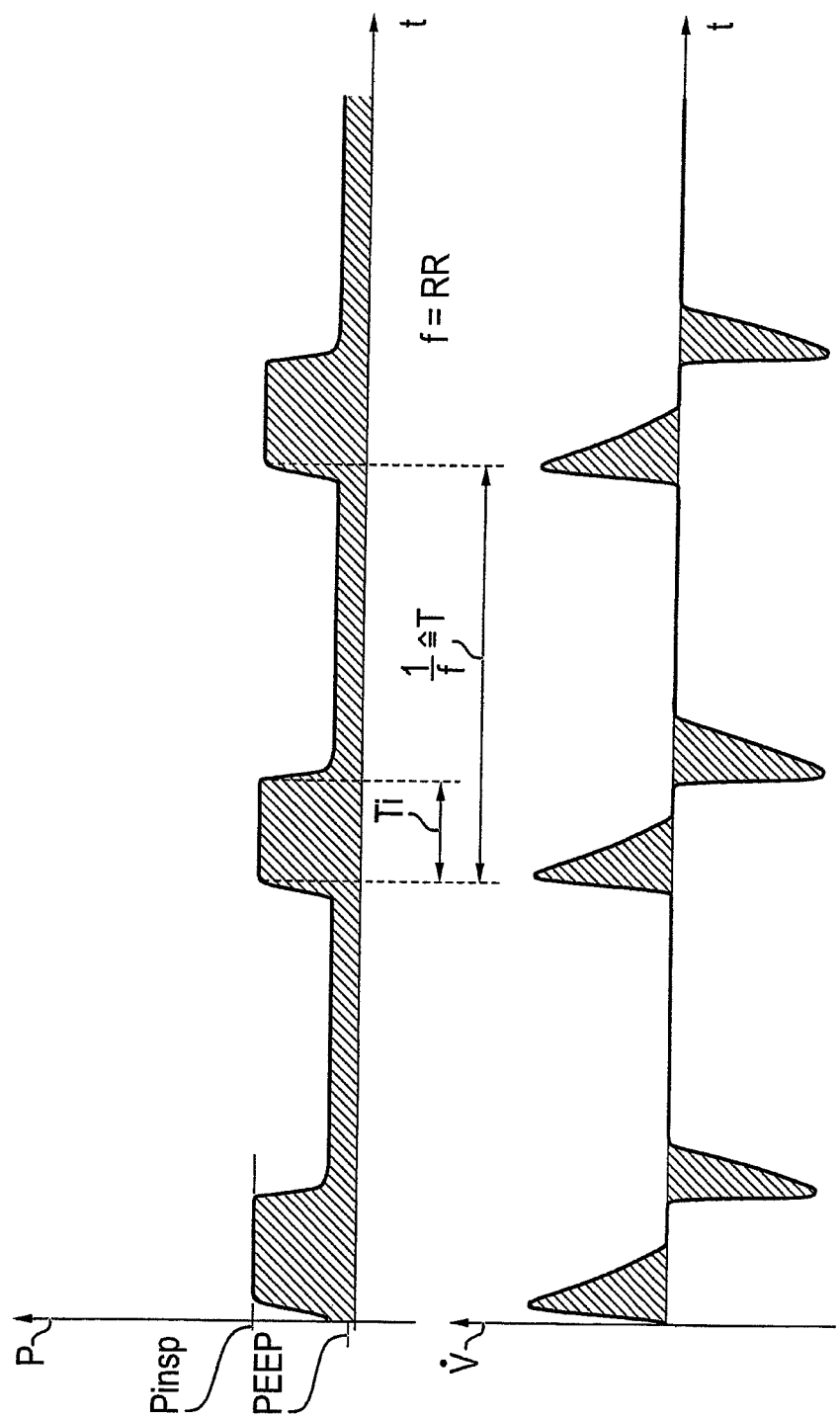
FIG. 2 is a graph view showing a pressure curve over time as well as a volume flow curve over time within the framework of a pressure control ventilation, during which no attempts at spontaneous breathing by a patient shall be made possible.

FIG. 2 shows a time curve P over time as well as a volume flow curve $\dot{V}$ in the course of a purely pressure control ventilation, during which the pressure is controlled during the inspiratory phases to a maximum pressure value Pinsp and during which the inspiratory phase is preset by a time period Ti. The rate for RR, with which the patient is ventilated, is preset here as a fixed value. Consequently, a time period T is obtained, which determines the time period between the respective starts of respective consecutive inspiratory phases.

Figure 3:
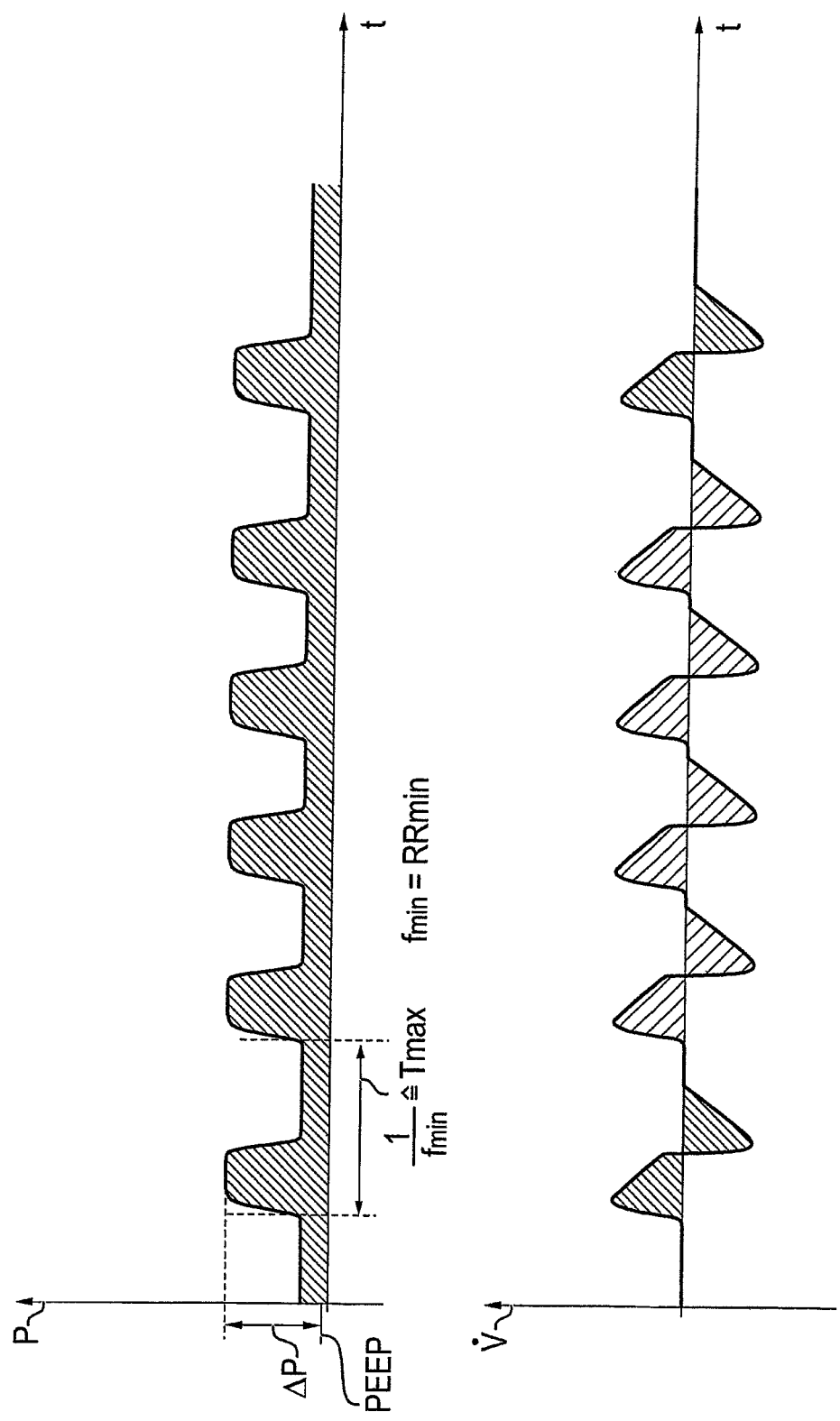
FIG. 3 is a graph view showing a pressure curve over time as well as a volume flow curve over time within the framework of a pressure support ventilation, which takes place within the framework of attempts at spontaneous breathing by a patient.

FIG. 3 shows a pressure curve P as well as a volume flow curve $\dot{V}$ within the framework of a purely pressure support ventilation. If the respiration rate of the patient drops below a certain minimum rate fmin or RRmin, a warning may preferably be outputted in the form of a warning signal. The maximum time period Tmax between the respective starts of respective inspiratory phases is thus preset by the minimum respiration rate fmin or RRmin The pressure P is increased during an inspiratory phase by a pressure stroke or desired pressure value ΔP during an inspiratory phase.

Figure 4:
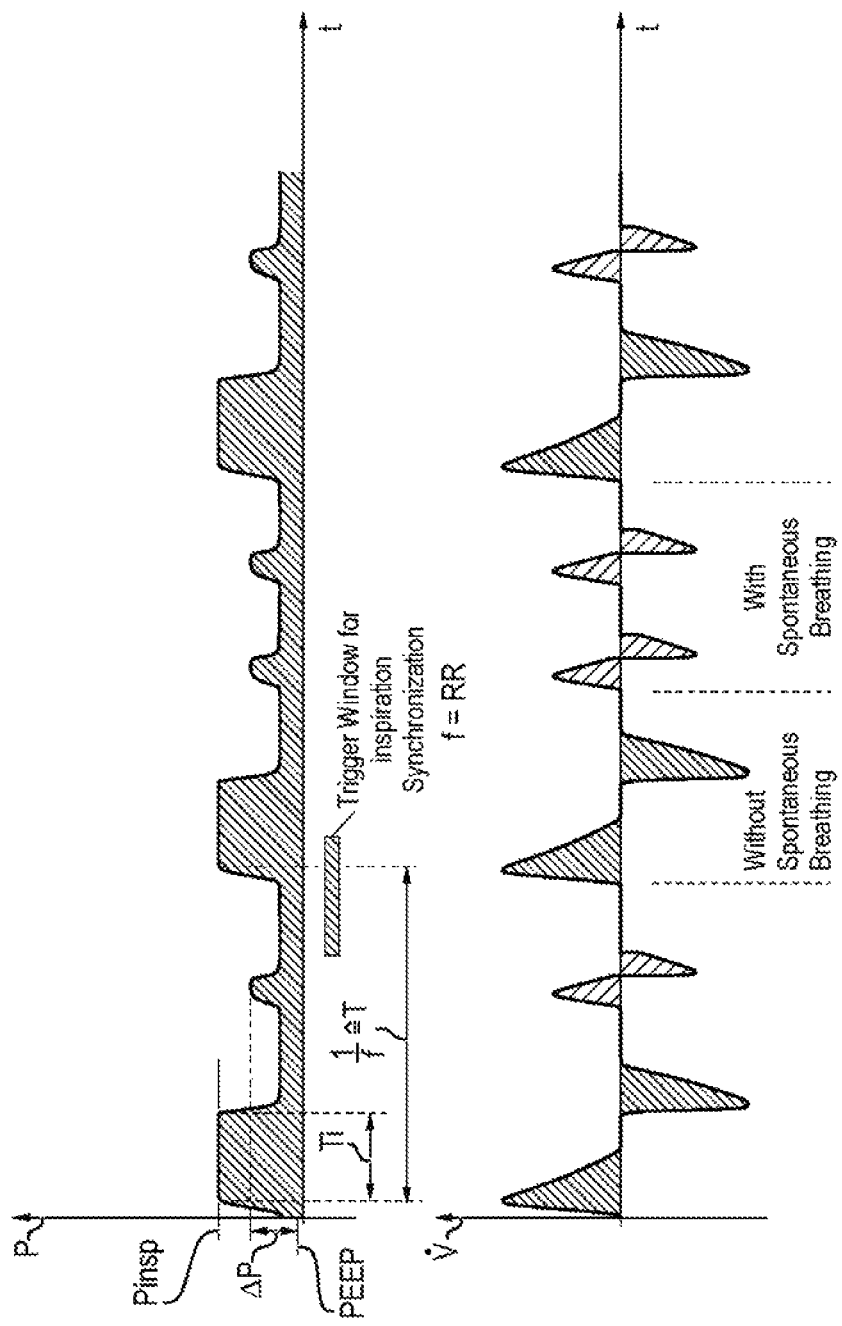
FIG. 4 is a graph view showing a pressure curve over time as well as a volume flow curve over time within the framework of a pressure control ventilation, during which attempts at spontaneous breathing by a patient are permitted.

FIG. 4 shows the principle of a pressure control ventilation, during which respective inspiratory phases with respective pressure supports can also be carried out based on spontaneous breathing of the patient.

The principles of pressure control ventilation and of pressure support ventilation can also be found in the German patent application "Ventilator and Process for the Automated Ventilation of a Patient," applicant: Drägerwerk AG & Co. KGaA, inventors: Stefan Mersmann, Wilfried Buschke, Prof. Christoph Höormann, filed with the German Patent and Trademark Office on Dec. 2, 2015 (DE 10 2015 015 439A). Furthermore, these principles are also explained in more detail in the documents "*Modes of Ventilation in Intensive Care,*" Karin Deden, Drager Medical GmbH, "*Zeus Infinity Empowered*" Manual, Dräger Medical AG & Co. KG, 1st edition, February 2009.

Figure 13:
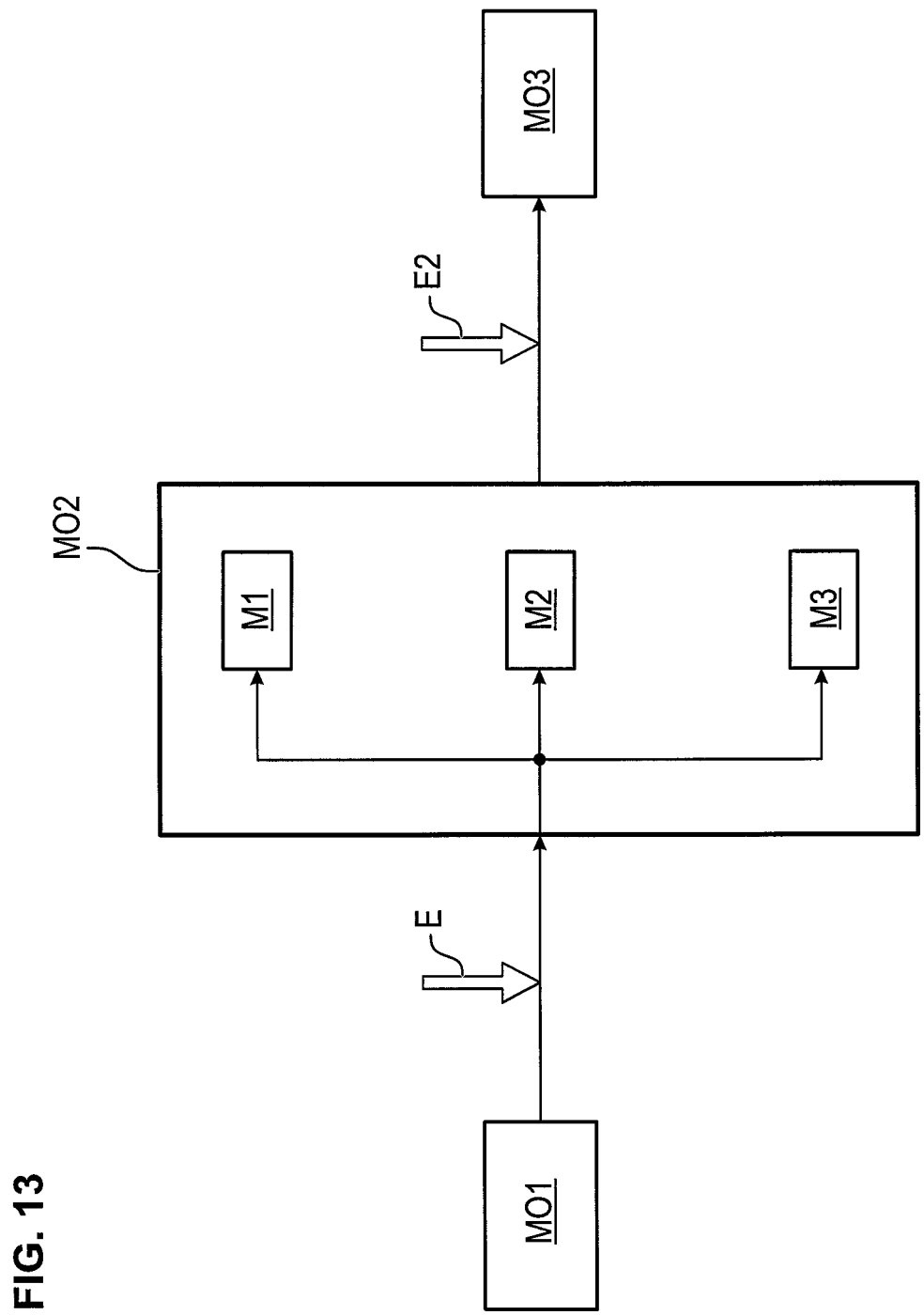
FIG. 13 is a schematic view showing different possible modes of operation.

FIG. 13 shows a review of different possible modes of operation, in which the anesthesia breathing gas being proposed can preferably be operated. In a first mode of operation MO1, a purely pressure control ventilation is carried out without attempts at spontaneous breathing by the patient being permitted. This type of ventilation was explained in more detail before with reference to FIG. 2. Further, a changeover to a second mode of operation MO2 is made possible if the presence of a desired operating state concerning the automated ventilation is detected. This is preferably possible when the operating state is detected within a preset time period. The changeover into the second operating mode MO2 then preferably takes place automatically. An output signal, which indicates the presence of the desired first operating state, is preferably outputted. There preferably is now a changeover into the second operating state MO2 when this is initiated by an input E by the clinician. The input E of the clinician preferably also represents a selection of which defined embodiment of different possible embodiments M1, M2 or M3 of the second mode of operation MO2 is then carried out. The different embodiments M1, M2, M3 are respective forms of automated ventilation, wherein a purely pressure control ventilation without attempts at spontaneous breathing by the patient being permitted is carried out in the first embodiment M1, wherein a pressure control ventilation with attempts at spontaneous breathing by the patient being permitted is, further, carried out in embodiment M2, and wherein a purely pressure support ventilation is, furthermore, carried out in the third embodiment M3 within the framework of attempts at spontaneous breathing by the patient.

In the second mode of operation MO2, a computer of the device carrying out the ventilation is configured to actuate a breathing gas delivery unit as a function of a detected pressure and of a preset desired pressure value, wherein the computer is further configured to perform an adaptation of the desired pressure value and an adaptation of a ventilation rate as a function of the detected volume flow and of a determined tidal volume and as a function of the carbon dioxide concentration or of a determined end-expiratory carbon dioxide concentration. Such embodiments M1, M2, M3 of a purely pressure control ventilation, of a pressure control ventilation with attempts at spontaneous breathing being permitted, as well as of a purely pressure support ventilation are described in detail in the German patent application "Ventilator and Process for the Automated Ventilation of a Patient," applicant: Drägerwerk AG & Co. KGaA, inventors: Stefan Mersmann, Wilfried Buschke, Prof. Christoph Hörmann, filed with the German Patent and Trademark Office on Dec. 2, 2015.

If it is now detected in the second mode of operation MO2 with the use of a process explained in more detail later on the basis of FIG. 8 that a second desired operating state concerning the automated ventilation is present, changeover is preferably carried out automatically from the second mode of operation MO2 into the third mode of operation MO3. A corresponding output signal, which indicates this presence of the second desired operating state, is preferably outputted. There preferably is a changeover from the second mode of operation MO2 into the third mode of operation MO3 as a function of another input E2 by the clinician. A purely pressure support ventilation is carried out in this third mode of operation MO3 within the framework of attempts at spontaneous breathing by the patient.

Figure 5:
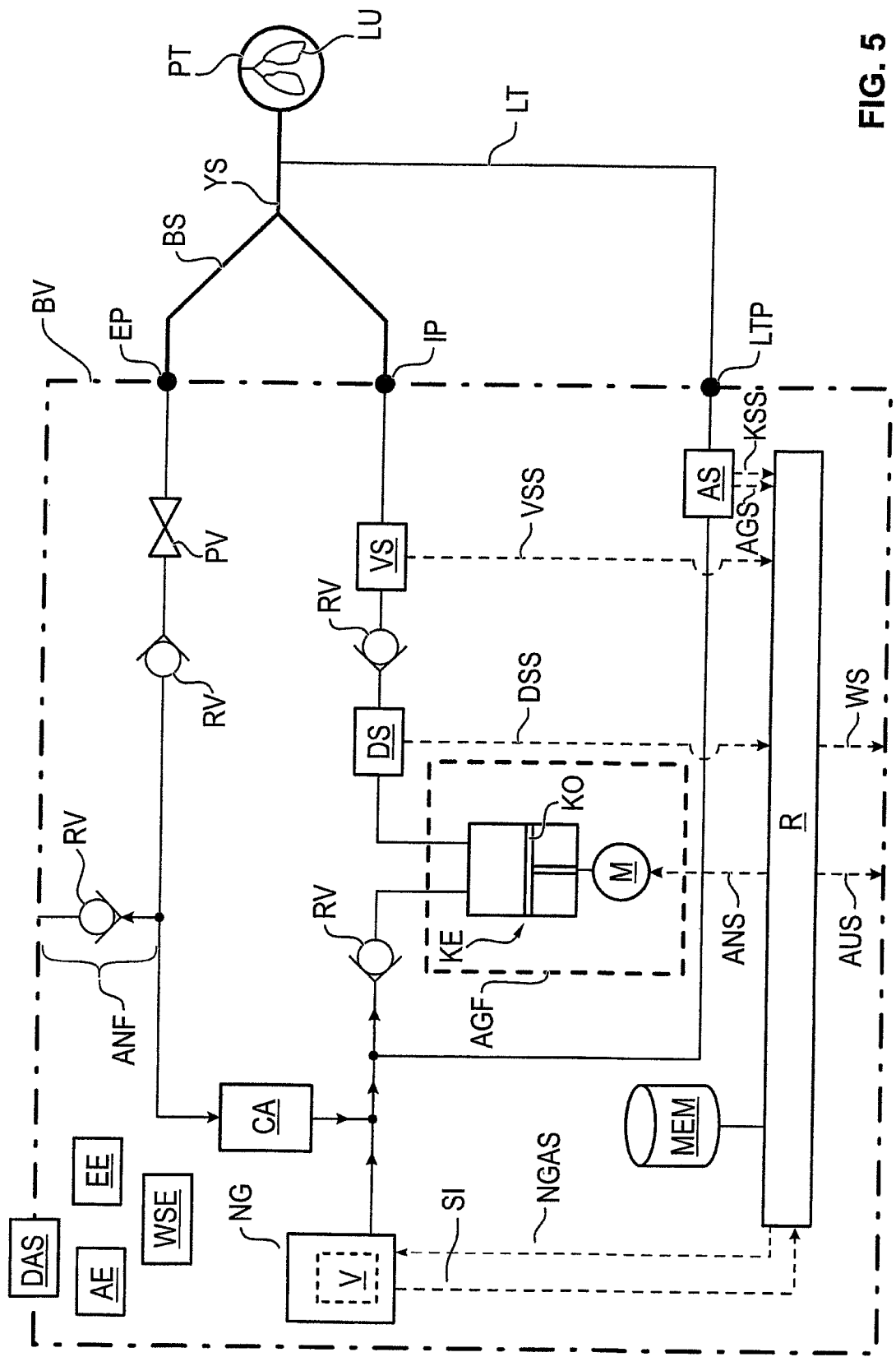
FIG. 5 is a schematic view showing an anesthetic ventilator according to the present invention.

FIG. 5 shows the anesthesia ventilator BV according to the present invention for the automated ventilation of a patient PT. The anesthesia ventilator BV according to the present invention has an inspiratory port IP and an expiratory port EP, to which a ventilation tube BS, which faces the patient PT, can be connected. A breathing gas is fed to the patient and is also removed from the patient to the device BV via this ventilation tube BS. The feeding is carried out via the inspiratory port IP, and the removal takes place via the expiratory port EP. The ventilation tube BS merges the connections of the ports EP, IP at a so-called Y-piece YS, which then usually ends at a tube, which is inserted into the patient PT in order to ventilate him via his lungs LU.

The anesthesia ventilator BV further has a breathing gas delivery unit AGF. The breathing gas delivery unit AGF is preferably a piston unit KE, in which a piston KO can be moved to and fro by a motor M.

The device BV further has at least one computer R, which may also be embodied by a network of a plurality of computers. The computer R is configured to actuate the breathing gas delivery unit AGF via an actuating signal ANS.

The anesthesia ventilator BV further has a pressure sensor DS for detecting a pressure of the breathing gas. The pressure sensor DS provides a pressure sensor signal DSS to the computer R.

The ventilator BV has at least one volume flow sensor VS for detecting a volume flow of the breathing gas. The volume flow sensor VS provides a volume flow sensor signal VSS to a computer R.

A minimum pressure PEEP is preferably generated by a valve PV, which is preferably located in the area of the expiratory port EP.

The anesthesia ventilator BV further has at least one breathing gas sensor AS. The sensor AS is preferably arranged behind a measuring line LT, which removes a measuring sample of the breathing gas at the Y-piece YS and is connected to the measured gas port LTP.

The at least one breathing gas sensor AS is configured to detect a carbon dioxide concentration in the breathing gas. The breathing gas sensor provides a carbon dioxide concentration signal KSS to the computer. The at least one breathing gas sensor AS is further preferably configured to detect an anesthetic gas concentration in the breathing gas. The breathing gas sensor preferably provides an anesthetic gas concentration signal AGS to the computer R. The at least one breathing gas sensor AS is preferably not an individual sensor but a sensor unit AS. Such a sensor unit AS has a plurality of sensors configured each specially for detecting the respective above-mentioned concentrations.

The anesthesia ventilator BV has a carbon dioxide absorber CA as well as an anesthetic gas-mixing unit NG. The anesthetic gas-mixing unit NG preferably has an anesthetic evaporator V. A gas mixture necessary for the anesthesia can then be introduced into the closed breathing circuit via the anesthetic gas-mixing unit NG. Such a gas mixture thus contains at least one anesthetic.

The anesthesia ventilator further has an anesthetic gas discharge line ANF or a connection to an anesthetic gas discharge line ANF.

The computer R controls the anesthetic gas-mixing unit NG by means of a control signal NGAS. The anesthetic gas-mixing unit NG preferably provides a status signal SI to the computer R, which signal indicates whether or not the anesthetic gas-mixing unit NG is introducing an anesthetic into the breathing gas. This status signal SI preferably indicates whether or not the anesthetic evaporator V is opened.

The gas flow within the anesthesia ventilator BV is preferably controlled by nonreturn valves RV.

The anesthesia ventilator BV from FIG. 5 has an input unit EE or an interface for an input unit EE, by means of which inputs, which can be made by an operator or clinician, can be received at the anesthesia ventilator BV.

The computer R preferably accesses a memory unit MEM in order to carry out the process according to the present invention.

The computer R preferably outputs a warning signal WS in the course of a purely pressure support ventilation to indicate the presence of a ventilation rate that is lower than a minimum ventilation rate. This output is preferably effected via a data interface DAS of the device BV. The device BV preferably has a warning signal output unit WSE itself, which can preferably output an optical and/or acoustic warning.

The computer R preferably outputs an output signal AUS, which indicates the presence of a detected operating state. This output preferably takes place via the data interface DAS to a display unit, not shown. The output preferably takes place via a display unit AE, which is part of the device BV.

The anesthesia ventilator BV according to the present invention is configured to carry out a purely pressure control ventilation of the patient PT in a first mode of operation. Further, the anesthesia ventilator BV according to the present invention is configured to carry out a ventilation according to one of the embodiments M1, M2 or M3, as described with reference to FIG. 13, in a second mode of operation.

Figure 6:
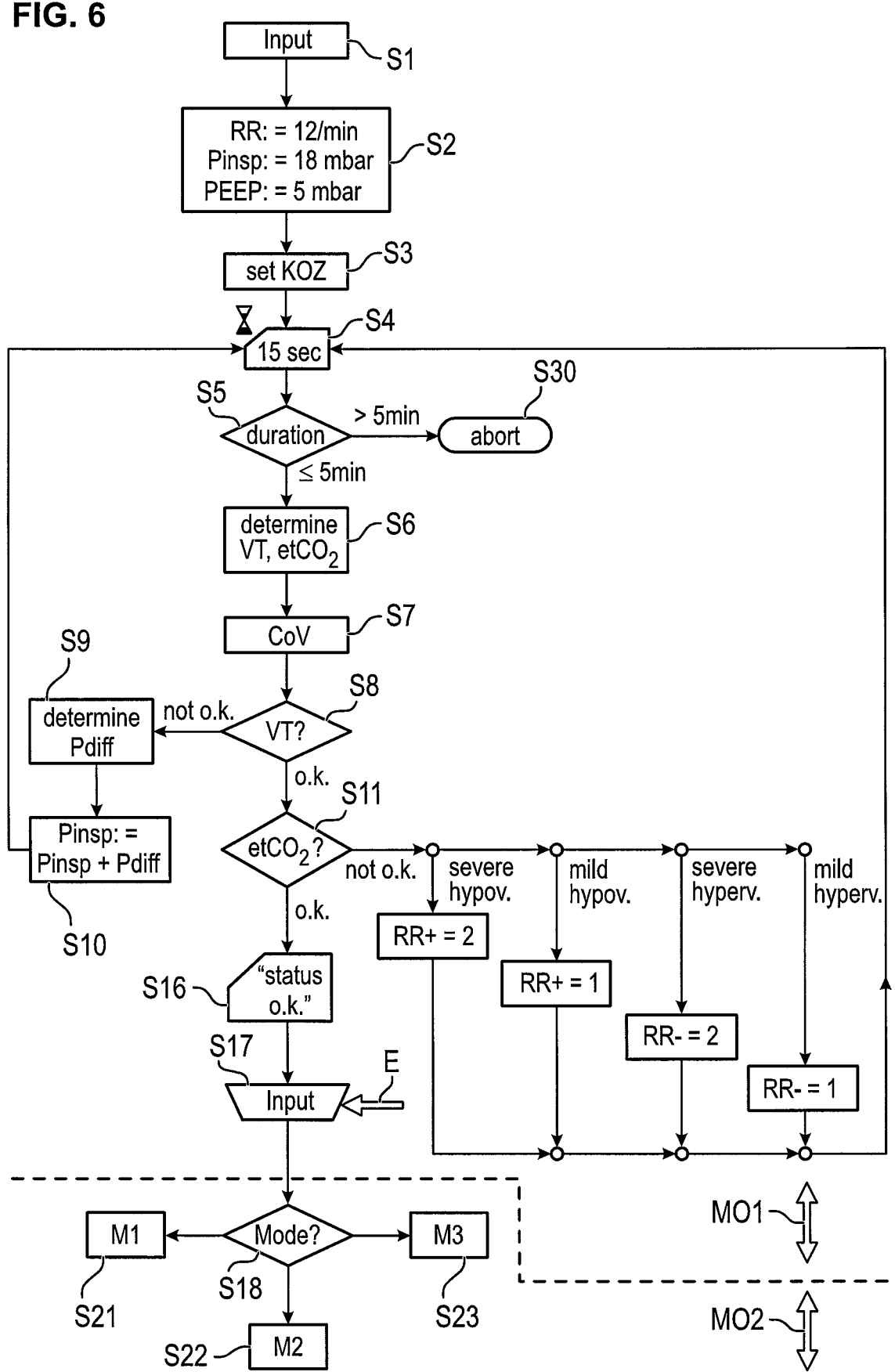
FIG. 6 is a flow diagram showing steps of the process according to the present invention in a first mode of operation and in a second mode of operation.

FIG. 6 shows initiation steps, by means of which the anesthesia ventilator BV from FIG. 5 can be prompted to carry out the process according to the present invention. Specifications are inputted in a step S1 by a user or clinician.

Figure 10:
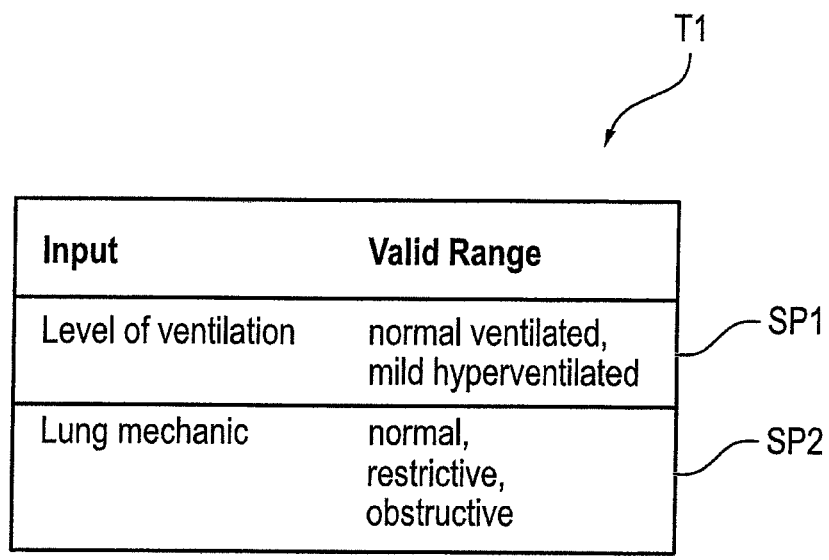
FIG. 10 is a table containing preset values that can be preset by a clinician.

In Table T1, FIG. 10 shows possibilities of different possible inputs or specifications within the framework of step S1 of FIG. 6. Different inputs or specifications, by means of which a desired degree of ventilation or a desired gas exchange rate of a patient can be selected, can be found in the first column SP1. These are preferably the variants of a normal ventilation or of a mild hyperventilation. Such inputs can be received through the interface EE or input unit EE of the anesthesia ventilator BV, which interface or input unit is shown in FIG. 5. This input unit EE may be an input unit in the form of a keyboard, a touchscreen and/or a computer mouse that belongs to or is in communication with the anesthesia ventilator BV.

The second column SP2 of FIG. 10 further contains different possibilities of inputs or specifications concerning lung property ("Lung Mechanic") of the patient. The specification may indicate a lung property of normal, restrictive or obstructive lungs.

Coming back to FIG. 6, initialization of ventilation-relevant parameters can now be carried out in step S2. The ventilation rate RR is preferably set now at 12 breaths per minute, the minimum pressure PEEP at 5 mbar, and the maximum pressure value Pinsp at 18 mbar. It is clear to the person skilled in the art that the values shown here are only exemplary values and may also be selected differently when embodying the process according to the present invention as well as when embodying the device according to the present invention.

Figure 7:
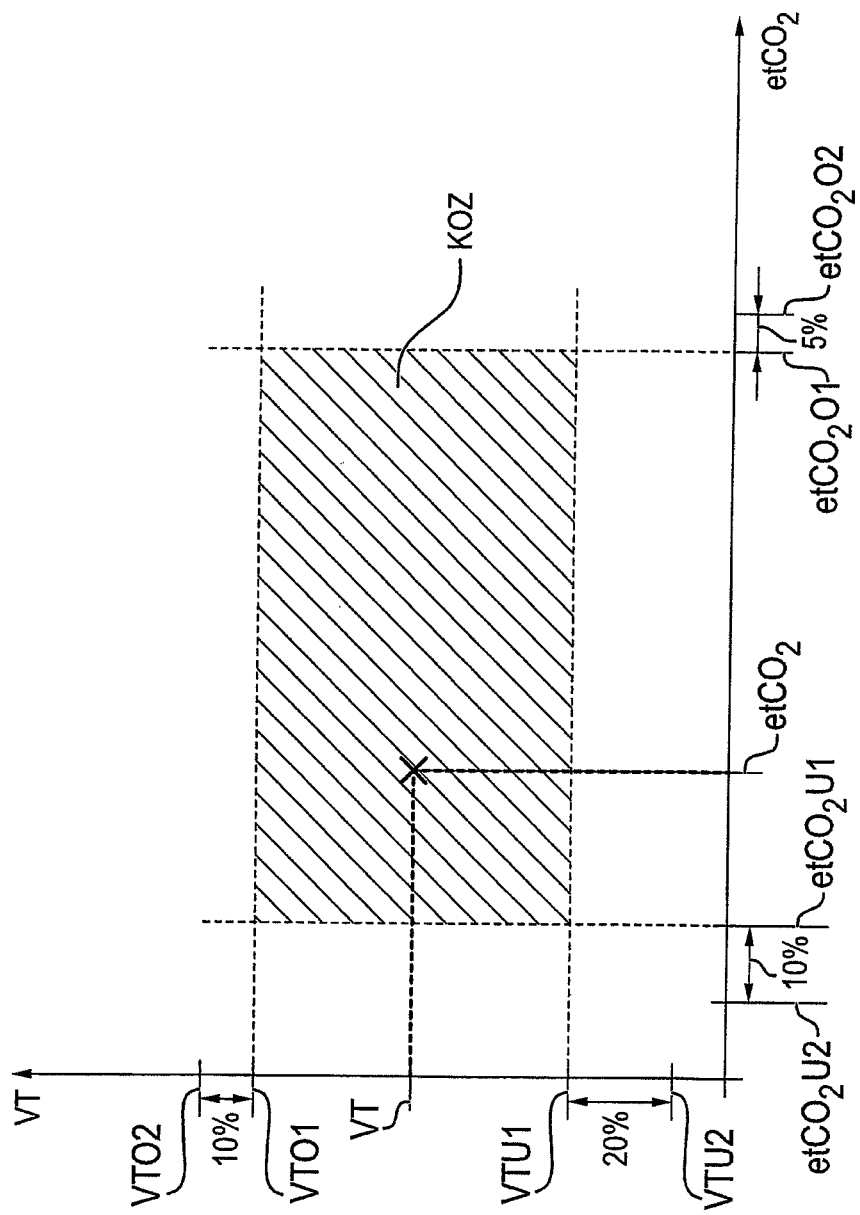
FIG. 7 is a graph view showing presettable limit values.

Limit values, which preferably indicate a so-called comfort zone KOZ, are defined in a process step S3. FIG. 7 can be examined corresponding to this step S3.

FIG. 7 indicates the comfort zone KOZ, which is given whenever a tidal volume VT inhaled by the patient that is between an upper volume limit value VTO1 and a lower volume limit value VTU1 is determined by the computer from the detected volume flow. Further, it is necessary for reaching the comfort zone KOZ that the end-expiratory carbon dioxide concentration etCO2 determined by the computer on the basis of the carbon dioxide concentration signal KSS be between an upper concentration limit value etCO2O1 and a lower concentration limit value etCO2U1.

An object of the process that is preferably to be reached is to ventilate the patient such that due to the ventilation, the patient has or breathes a tidal volume VT that is within the volume limit values VTO1, VTU1, and also generates at the same time an end-expiratory carbon dioxide concentration etCO2 that is within the concentration limit values etCO2U1 and etCO2O1.

Figure 11:
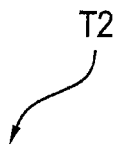
FIG. 11 is a table containing possible limit values for carrying out the process according to the present invention.

Adding FIG. 11 and taking table T2 into consideration, it can be determined from FIG. 6 with reference to step S3 how the respective volume limit values VTO1, VTU1 as well as the respective concentration limit values etCO2U1, etCO2O1 can be selected by selecting the specifications concerning the lung property ("Lung Mechanic") of the patient as well as the gas exchange rate or the degree of ventilation ("normal ventilated"—normally ventilated / "mild hyperventilated"—mildly hyperventilated).

Based on the detected volume flow, the computer R of FIG. 5 determines a tidal volume VT inhaled by the patient. The computer preferably determines for this the tidal volume as an integral value of the volume flow over this duration Ti on the basis of the detected volume flow and of the duration Ti of the inspiratory phase. As an alternative, a duration of an inspiratory phase can be determined by inferring a start of the inspiratory phase when a volume flow threshold value is exceeded and an end of the inspiratory phase when the volume flow threshold value is fallen below.

Based on the detected carbon dioxide concentration, the computer determines an end-expiratory carbon dioxide concentration etCO2. The end of an end-expiratory phase is then preferably inferred by comparing the volume flow, as is shown in FIG. 1, and a lower or negative USW threshold value when the detected volume flow passes through the lower threshold value from below.

The values determined by the computer R for the tidal volume as well as the end-expiratory carbon dioxide concentration are preferably provided as measured values every 4 sec.

There is at first a waiting period of 15 sec according to step S4 of FIG. 6.

It is then checked in process step S5 whether the first mode of operation MO1 has already lasted for a maximum time period of preferably longer than 5 minutes or less than the maximum time period. If the preset maximum time period of preferably 5 minutes is exceeded, the process proceeds further to a process step S30, in which the process is preferably interrupted. Consequently, if no desired operating state concerning the automated ventilation was detected during a preset maximum time period, preferably 5 minutes, a transition from the first mode of operation MO1 to the second mode of operation MO2 is not made possible. An output signal, which indicates that the desired operating state could not be reached within the maximum time period, is preferably outputted by the computer. This can possibly be interpreted by the clinician as an indication that the patient has no adequate breathing characteristic within the preset time period to be ventilated in a stable manner by means of the second mode of operation.

If the duration of the first mode of operation MO1 is shorter than the preset time period of preferably 5 minutes, the process is continued to process step S6.

The tidal volume VT taken into consideration is then determined within the framework of step S6 by means of a preprocessing, preferably a median filtering, of the measured values of the tidal volume that were present or measured in the last 60 sec. The end-expiratory carbon dioxide concentration etCO2 taken into consideration is likewise determined by means of a preprocessing, preferably a median filtering, on the basis of the measured values of the end-expiratory carbon dioxide concentration that represent the last 60 sec or were measured within the last 60 sec.

After determining the tidal volume VT as well as the end-expiratory carbon dioxide concentration etCO2, a degree of ventilation is determined with reference to the tidal volume within the framework of step S7 and, further, a degree of ventilation is determined with reference to the end-expiratory carbon dioxide concentration.

FIG. 12, which shows in Table T3 various degrees of ventilation with comparison of the tidal volume VT with the previously determined limit values, shall be used for this. Not only the upper and lower limit value VTO1, VTU1, respectively, as shown before in Table T2, but additional, second limit values VTO2, VTU2, are used here as well. These second limit values VTO2, VTU2 are likewise shown in FIG. 7. Consequently, respective second limit values VTO2, VTU2, in which a deviation by 10% or 20% from the first limit values VTO1, VTU2 is taken into consideration, are used.

Corresponding statements may also be made concerning the degree of ventilation with reference to the end-expiratory carbon dioxide concentration compared to the concentration values etCO2U1, etCO2O1 as well as additional, second concentration values etCO2U2, etCO2O2, which deviate by 5% and 10%, respectively, from the first concentration values etCO2U1, etCO2O1 and are likewise shown in FIG. 7. Consequently, a degree of ventilation can be determined with reference to end-expiratory carbon dioxide concentration on the basis of Table T4 of FIG. 12.

It is then checked in process step S8 whether the determined tidal volume VT is within the volume limit values. In other words, it is checked whether the measured tidal volume is between the upper limit value VTO2 and the lower limit value VTU1. If not, the process is branched off to a process step S9, in which the desired pressure value Pinsp is then adapted jointly with the process step S10.

A desired pressure change Pdiff is determined in process step S9. A minute volume MV suitable for the particular patient, $$MV = RR * VT,$$

can possibly be obtained with this pressure change Pdiff.

This is carried out by a target tidal volume TVT being preset. This preferably depends on the upper volume limit value VTO1 and the lower volume limit value VTU1 according to $$TVT := (VTO1 - VTU1)/2.$$

Based on a preset pressure adaptation value DEP, the target tidal volume TVT as well as the measured tidal volume VT, the desired pressure change Pdiff can now be determined in step S10. This is carried out according to $$Pdiff := ((TVT - VT) * DEP)/VT.$$

The adaptation of the desired pressure value Pinsp is then performed in step S10, preferably according to $$Pinsp := Pinsp + Pdiff.$$

The process then returns to process step S4.

If the checking in process step S8 revealed that the measured tidal volume VT was already within the preset volume limit values, i.e., within the comfort zone range KOZ, the process proceeds further to a process step S11, in which the end-expiratory carbon dioxide concentration etCO2 is then checked.

If the checking in process step S11 revealed that the end-expiratory carbon dioxide concentration etCO2 was not within the concentration limit values or the comfort zone KOZ shown in FIG. 7, the process is branched off to the further process steps S12 through S15, which perform an adaptation of the respiration rate RR. In other words, if the measured end-expiratory carbon dioxide concentration etCO2 is not between the lower carbon dioxide limit value etCO2U1 and the upper carbon dioxide limit value etCO2O1, the ventilation rate RR is adapted.

Then, when branching off from step S11 to steps S12 through S15, it is first determined with the use of Table 4 in FIG. 12 whether a degree of hyperventilation, a normal degree of ventilation or a degree of hypoventilation of the patient is present. The corresponding state of the patient can then be determined based on the entries in Table T4. This state depends on the measured end-expiratory carbon dioxide concentration etCO2 as well as the corresponding limit values etCO2U2, etCO2U1, etCO2O1, etCO2O2.

If a severe hypoventilation ("severe hypoventilated") is present, the ventilation rate RR is adapted in process step S12 such that this is increased by the value of 2 per minute.

Corresponding adaptations are performed as a function of the corresponding degrees of ventilation mild hypoventilation, mild hyperventilation as well as severe hyperventilation correspondingly in the alternative process steps S13, S14 or S15. After adaptation of the ventilation rate in one of the steps S12 through S15, the process is branched back to process step S4.

If the checking of the tidal volume VT in process step S8 as well as the checking of the end-expiratory carbon dioxide concentration etCO2 in process step S11 revealed that both values are within the corresponding limit values VT_O1, VT_U1, etCO2U1, etCO2O1 and within the comfort zone KOZ, it may be assumed that the desired operating state concerning the automated ventilation is present and this is thus detected by passing over from step S11 to the further steps S16, etc. The process is then branched off from process step S11 to process step S16, in which an output signal ("Status o.k."), which indicates the presence of the desired operating state, is outputted.

An input signal E of a clinician is then waited for in a process step S17. If this input E of the clinician is present, the process is then preferably changed over into a second mode of operation MO2. The transition from step S11 to step S18 preferably takes place without checking for an input signal E in step S17.

The input E preferably indicates a selection of a preferred embodiment M1, M2, or M3 of a corresponding form of ventilation, which were explained in more detail before with reference to FIG. 13. The process can then be branched off to one of the embodiments M1, M2 or M3 or to the corresponding steps S21, S22 or S23 in a second mode of operation MO2, preferably in a substep S18, depending on the input E of the clinician.

Further, a detection process, which will now be explained in more detail with reference to FIG. 8, can be carried out in the second mode of operation MO2 simultaneously with a ventilation process according to one of the embodiments M1, M2 or M3.

Figure 8:
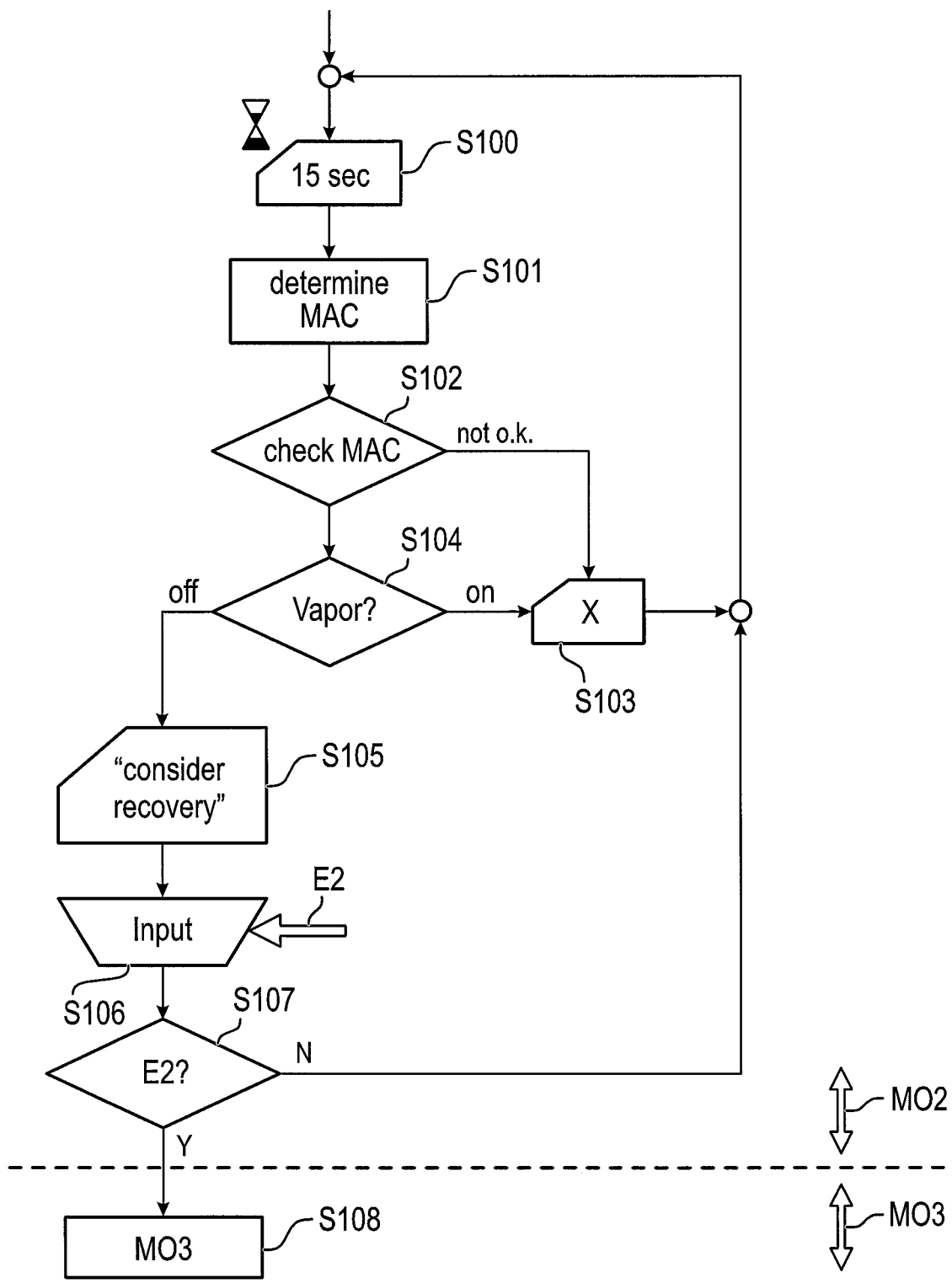
FIG. 8 is a flow diagram showing steps that are carried out in the course of a second mode of operation as well as a transition to a mode of operation.

FIG. 8 shows partial process steps, which illustrate a process, which can be carried out continuously in the course of the second mode of operation in order to detect the presence of a second desired operating state concerning the automated ventilation. This is preferably an operating state that can indicate for a clinician that the patient has a stable breathing activity from the viewpoint of the clinician, so that the clinician can bring about a third mode of operation with a pressure support ventilation, preferably by an additional input E2.

An anesthetic gas concentration in the breathing gas is taken into consideration for the detection of the second operating state.

There is a waiting period for a time period of 15 sec in a first partial process step S100.

A mean alveolar anesthetic gas concentration is then determined in a partial process step S101. Such a mean alveolar anesthetic gas concentration is also called "minimum alveolar concentration." This mean alveolar anesthetic gas concentration MAC is preferably a standardized variable xMAC or a MAC multiple, as is disclosed in the document "*Primus Infinity Empowered,*" Dräger Medical GmbH, Edition: Mar. 9, 2010, pp. 132-134.

Such a mean alveolar anesthetic gas concentration MAC is determined over an averaged time window of past measured values, which are indicated by the anesthetic gas concentration signal AGS, see FIG. 5.

The computer determines for this the concentration of the anesthetic gas preferably during an end-expiratory phase on the basis of the anesthetic gas concentration signal AGS in FIG. 5. The computer R may preferably use for this the presence of an expiratory phase EXP from FIG. 1, using the lower threshold value USW in the aforementioned and above-described manner.

It is then checked in partial step S102 of FIG. 8 whether a time curve of the determined mean alveolar anesthetic gas concentration over time meets preset conditions.

Figure 9:
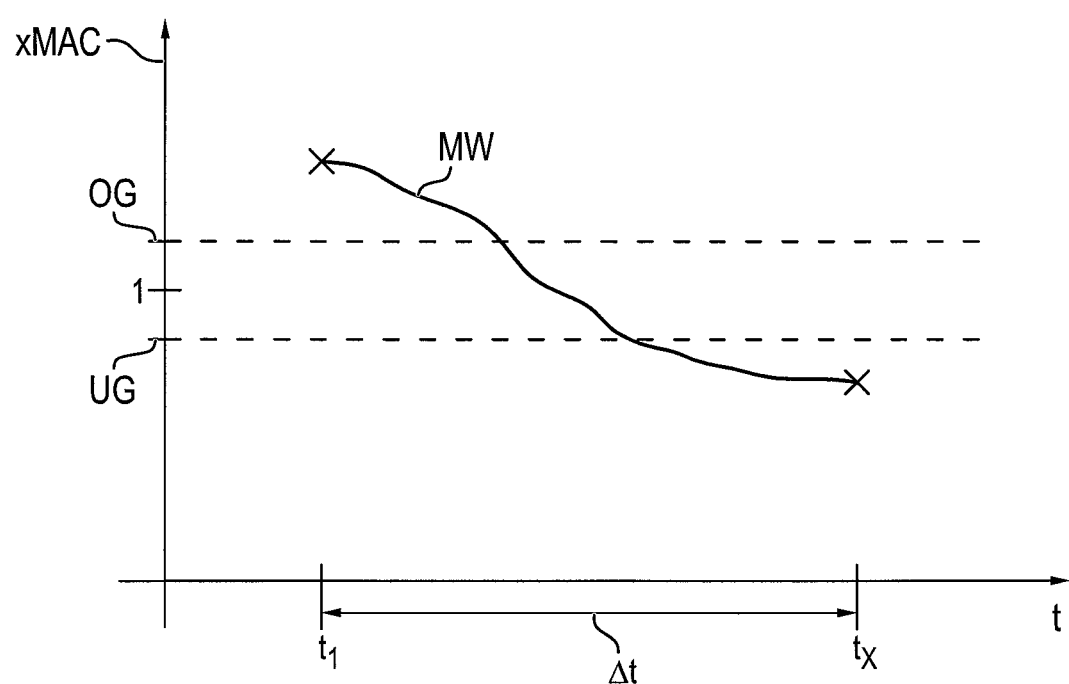
FIG. 9 is a graph view showing a curve of a mean alveolar anesthetic gas concentration over time.

FIG. 9 illustrates for this such a checking of the time curve of the mean alveolar anesthetic gas concentration MAC over the time t. Measured values MW are taken into consideration for a current time tX as well as for a time t1 preceding it by a time interval ?t. The mean alveolar anesthetic gas concentration MAC is preferably the aforementioned anesthetic gas concentration xMAC.

If the mean alveolar anesthetic gas concentration xMAC is above an upper limit value OG, which is preferably the value 1.1, for the past time tl, and if the mean alveolar anesthetic gas concentration xMAC is below a lower limit value UGU, which is preferably the value 0.9, an adequate reduction of the mean alveolar anesthetic gas concentration xMAC is assumed. This is a reduction over time of the mean alveolar anesthetic gas concentration, as it is to be expected during the termination of an anesthesia ventilation, during which no more anesthetic gas is introduced into the breathing gas by the anesthetic gas-mixing unit NG according to FIG. 5.

If the mean alveolar anesthetic gas concentration meets the required condition in partial process step S102 over time, the process is branched off to a process step S104, in which an operating state of the anesthetic evaporator is checked further as a part of the anesthetic gas-mixing unit NG according to FIG. 5.

If the anesthetic evaporator is still switched on, it cannot necessarily be expected that the anesthesia of the patient shall indeed be terminated, so that the process will then branch off from step S104 to a process step S103.

A possibly outputted message, for example, a message ("Consider Recovery") from process step S105, is canceled in process step S103. The process is also branched off directly from process step S102 to process step S103 in the case in which the checking of the mean alveolar anesthetic gas concentration was not satisfactory in process step S102.

The process returns from process step S103 to process step S100.

If it is detected in process step S104 that the anesthetic evaporator is configured, it is inferred that the second operating state is present and this is thus detected. An output signal, which indicates that the presence of the second, desired operating state is present ("Consider Recovery"), is then preferably outputted in process step S105. Consequently, a so-called recovery phase of the patient may be considered by the clinician. A purely pressure support ventilation is then preferably carried out as a third mode of operation MO2 in such a recovery phase.

If an additional input signal E2 is preferably inputted by the clinician in process step S106, the process then proceeds in step S107 to the third mode of operation MO3 or to process step S108.

If the second operating state is detected, there preferably is an automatic changeover from the second mode of operation MO2 to the third mode of operation MO3, without dependence on an input signal E2 by a user or clinician. Consequently, the process then proceeds directly from step S104 to step S108.

In the third mode of operation MO3 the computer actuates the breathing gas delivery unit as a function of the detected pressure and of a preset desired pressure value within the framework of a purely pressure support ventilation. The computer now performs an adaptation of the desired pressure value $\Delta P$ as a function of the detected anesthetic gas concentration. How the computer can perform the adaptation of the desired pressure value as a function of the detected anesthetic gas concentration is explained in detail in the application Anesthesia Ventilator for the Automatic Ventilation of a Patient, Applicant: Drägerwerk AG & Co. KGaA, inventors: Stefan Mersmann, Wilfried Buschke, Prof Christoph Hörmann, filed with the German Patent and Trademark Office on Dec. 2, 2015 (DE 10 2015 015 440A).

Even though some aspects were described in connection with a device, it is obvious that these aspects also represent a description of the corresponding process, so that a block or a component of a device can also be defined as a corresponding process step or as a feature of a process step. Analogously hereto, aspects that were described in connection with a process step or as a process step also represent a description of a corresponding block/step or detail or feature of a corresponding device, and the device or the corresponding computer is configured to carry out the process step.

The computer R shown in FIG. 5 is to be considered to be at least one computer. An implementation of at least one computer R may also be embodied by a combination of a plurality of computers, preferably by the use of software in connection with hardware. Depending on certain implementation requirements, exemplary embodiments of the present invention may be implemented in hardware and/or in software. The implementation may be carried out with the use of a digital storage medium, for example, a floppy disk, a DVD, a Blu-Ray disk, a CD, a ROM, a PROM, an EPROM, an EERPROM or a FLASH memory, a hard drive or another magnetic or optical memory, on which electronically readable control signals, which can or do interact with a programmable hardware component such that the respective process is carried, are stored.

A programmable hardware component may be formed by a processor, a computer processor (CPU=Central Processing Unit), a graphics processor (GPU=Graphics Processing Unit), a computer, a computer system, an application-specific integrated circuit (ASIC=Application-Specific Integrated Circuit), an integrated circuit (IC=Integrated Circuit), a System on Chip (SOC), a programmable logic component or a field-programmable gate array with a microprocessor (FPGA=Field Programmable Gate Array).

The digital storage medium may therefore be machine- or computer-readable. Some exemplary embodiments consequently comprise a data storage medium, which has electronically readable control signals, which are capable of interacting with a programmable computer system or with a programmable hardware component such that one of the processes being described here is carried out. An exemplary embodiment is consequently a data storage medium (or a digital storage medium or a computer-readable medium), on which the program for carrying out one of the processes being described here is recorded.

Exemplary embodiments of the present invention may generally be implemented as program, firmware, computer program or computer program product with a program code or as data, wherein the program code or the data act so as to carry out one of the processes when the program is running on a processor or on a programmable hardware component. The program code or the data may also be stored, for example, on a machine-readable medium or data storage medium. The program code or the data may occur, among other things, as source code, machine code or byte code as well as as other intermediate code.

A further exemplary embodiment is, furthermore, a data stream, a signal sequence or a sequence of signals, which data stream or sequence represents the program for carrying out one of the processes described herein. The data stream, the signal sequence or the sequence of signals may be configured, for example, such as to be transferred via a data communication link, for example, via the Internet or another network. Exemplary embodiments are thus also signal sequences representing data, which are suitable for transmission via a network or a data communication link, wherein the data represent the program.

A program according to an exemplary embodiment may implement one of the processes during its execution, for example, by reading storage locations or by writing a datum or a plurality of data into these, wherein switching operations or other operations are optionally brought about in transistor structures, in amplifier structures or in other electrical, optical, magnetic components or components operating according to another principle of action. Data, values, sensor values or other information can correspondingly be detected, determined or measured by reading a storage location. A program can therefore detect, determine or measure variables, values, measured variables and other information by reading one or more storage locations as well as bring about, prompt or carry out an action as well as actuate other devices, machines and components by writing to one or more storage locations.

While specific embodiments of the invention have been shown and described in detail to illustrate the application of the principles of the invention, it will be understood that the invention may be embodied otherwise without departing from such principles.

The invention claimed is:

1. An anesthesia ventilator for the automated ventilation of a patient, the anesthesia ventilator comprising:
    an expiratory port and an inspiratory port for connecting a ventilation tube for supplying a breathing gas to the patient;
    a breathing gas delivery unit;
    at least one volume flow sensor for detecting a volume flow of the breathing gas;
    at least one breathing gas sensor for detecting a carbon dioxide concentration;
    at least one pressure sensor for detecting a pressure of the breathing gas; and
    a computer configured:
    to actuate the breathing gas delivery unit in a first mode of operation as a function of a preset ventilation rate, of the detected pressure and of a preset desired pressure value;
    to detect a presence of a desired operating state concerning the automated ventilation in the first mode of operation on the basis of the detected volume flow and of the detected carbon dioxide concentration; and to, upon detecting the desired operating state, initiate a changeover to a second mode of operation, in which the computer actuates the breathing gas delivery unit such that a pressure control ventilation or a pressure support ventilation is carried out, wherein the computer is further configured, in the first mode of operation, to:

determine a tidal volume fed to the patient on the basis of the detected volume flow;

determine an end-expiratory carbon dioxide concentration on the basis of the detected carbon dioxide concentration; and perform an adaptation of the desired pressure value and an adaptation of the ventilation rate as a function of:

the determined tidal volume;
an upper volume limit value;
a lower volume limit value;
the determined end-expiratory carbon dioxide concentration;
an upper concentration limit value; and
a lower concentration limit value.

2. The anesthesia ventilator in accordance with claim 1, wherein the computer is configured to make possible the changeover to the second mode of operation when the operating state is detected within a preset time period.

3. The anesthesia ventilator in accordance with claim 2, wherein the computer is configured automatically to perform the changeover to the second mode of operation when the operating state is detected within the preset time period.

4. The anesthesia ventilator in accordance with claim 1, wherein the computer is configured to:
output an output signal, which indicates the presence of the desired operating state; and
change over to the second mode of operation as a function of an input signal when the operating state is detected.

5. The anesthesia ventilator in accordance with claim 1, wherein the at least one breathing gas sensor is further configured to detect an anesthetic gas concentration in the breathing gas, wherein the desired operating state is a first desired operating state, wherein the computer is further configured to:
detect the presence of a second desired operating state concerning the automated ventilation on the basis of the detected anesthetic gas concentration; and
output, when the second operating state is detected, an output signal, which indicates the presence of the second desired operating state, in the second mode of operation.

6. The anesthesia ventilator in accordance with claim 5, wherein the computer is further configured to detect the presence of the second desired operating state in the second mode of operation as a function of an information signal, which indicates an operating state of an anesthetic evaporator.

7. The anesthesia ventilator in accordance with claim 5, wherein the computer is configured to change over into a third mode of operation, in which the computer actuates the breathing gas delivery unit such that a pressure support ventilation is carried out, in case the second operating state is detected, as a function of an additional input signal or else automatically.

8. The anesthesia ventilator in accordance with claim 5, wherein the computer is further configured, in the second mode of operation, to:
actuate the breathing gas delivery unit for a pressure control ventilation or for a pressure support ventilation as a function of the detected pressure and of a second preset desired pressure value;

determine a tidal volume fed to the patient on the basis of the detected volume flow;

determine an end-expiratory carbon dioxide concentration on the basis of the detected carbon dioxide concentration in the second mode of operation;

perform an adaptation of the desired pressure value and an adaptation of a ventilation rate as a function of:
the determined tidal volume;
an upper volume limit value;
a lower volume limit value;
the determined end-expiratory carbon dioxide concentration;
an upper concentration limit value; and
a lower concentration limit value.

9. The anesthesia ventilator in accordance with claim 7, wherein the computer is further configured to:
actuate the breathing gas delivery unit in the third mode of operation as a function of the detected pressure and of a preset desired pressure value; and
perform an adaptation of the desired pressure value as a function of the detected anesthetic gas concentration in the third mode of operation.

10. A process for operating an anesthesia ventilator for an automated ventilation of a patient, the process comprising the steps of:
feeding of a breathing gas to a patient via an inspiratory port and returning the breathing gas via an expiratory port by operating a breathing gas delivery unit;
detecting a volume flow of the breathing gas by means of at least one volume flow sensor;
detecting a carbon dioxide concentration of the breathing gas by means of at least one breathing gas sensor;
detecting a pressure of the breathing gas by means of at least one pressure sensor;
in a first mode of operation, actuating the breathing gas delivery unit as a function of a preset ventilation rate, of the detected pressure and of a preset desired pressure value by means of a computer;
in the first mode of operation, detecting the presence of a desired operating state concerning the automated ventilation of the patient on the basis of the detected volume flow and of the detected carbon dioxide concentration;
in the first mode, determining a tidal volume fed to the patient on the basis of the detected volume flow via the computer;
in the first mode, determining an end-expiratory carbon dioxide concentration on the basis of the detected carbon dioxide concentration via the computer;
in the first mode, performing an adaptation of the desired pressure value and an adaptation of the ventilation rate via the computer as a function of:
the determined tidal volume;
an upper volume limit value;
a lower volume limit value;
the determined end-expiratory carbon dioxide concentration;
an upper concentration limit value; and
a lower concentration limit value;
upon detecting the operating state initiating a changeover into a second mode of operation, in which the computer actuates the breathing gas delivery unit such that a pressure control ventilation or a pressure support ventilation is carried out.

11. A computer device for an anesthesia ventilator for an automated ventilation of a patient, the computer device comprising a computer, wherein the computer is configured:
- to receive a volume flow signal, which indicates a volume flow of a breathing gas;
- to receive a carbon dioxide concentration signal, which indicates a carbon dioxide concentration in the breathing gas;
- to receive a pressure signal, which indicates a pressure of the breathing gas;
- to provide, in a first mode of operation, an actuating signal for a breathing gas delivery unit, wherein the computer determines the actuating signal as a function of a preset ventilation rate, of the received pressure signal and of a preset desired pressure value;
- to determine, in the first mode of operation, the presence of a desired operating state concerning the automated ventilation in the first mode of operation on the basis of the received volume flow and of the received carbon dioxide concentration; and
- upon determining the desired operating state to initiate a changeover to a second mode of operation, in which the computer actuates the breathing gas delivery unit such that a pressure control ventilation or a pressure support ventilation is carried out, wherein the computer, in the first mode of operation, is further configured to:
- determine a tidal volume fed to the patient on the basis of the received volume flow;
- determine an end-expiratory carbon dioxide concentration on the basis of the carbon dioxide concentration; and
- perform an adaptation of the desired pressure value and an adaptation of the ventilation rate as a function of:
- the determined tidal volume;
- an upper volume limit value;
- a lower volume limit value;
- the determined end-expiratory carbon dioxide concentration;
- an upper concentration limit value; and
- a lower concentration limit value.

12. A process for operating an anesthesia ventilator for the automated ventilation of a patient, the process comprising the steps of:
- detecting a volume flow signal, by at least one volume flow sensor, indicating a volume flow of a breathing gas;
- detecting a carbon dioxide concentration signal, by at least one breathing gas sensor, indicating a carbon dioxide concentration in the breathing gas;
- detecting a pressure signal, by at least one pressure sensor, indicating a pressure of the breathing gas;
- in a first mode of operation, providing an actuating signal for a breathing gas delivery unit, wherein a computer determines the actuating signal as a function of a preset ventilation rate, of the detected pressure signal and of a preset desired pressure value;
- in the first mode of operation detecting a presence of a desired operating state concerning the automated ventilation of the patient on the basis of the detected volume flow and of the detected carbon dioxide concentration;
- in the first mode, determining a tidal volume fed to the patient on the basis of the detected volume flow via the computer;
- in the first mode, determining an end-expiratory carbon dioxide concentration on the basis of the detected carbon dioxide concentration via the computer;
- in the first mode, performing an adaptation of the desired pressure value and an adaptation of the ventilation rate as a function of:
- the determined tidal volume;
- an upper volume limit value;
- a lower volume limit value;
- the determined end-expiratory carbon dioxide concentration;
- an upper concentration limit value; and
- a lower concentration limit value;
- if the presence of the desired operating state is detected, making possible a changeover to a second mode of operation, in which the computer actuates the breathing gas delivery unit such that a pressure control ventilation or a pressure support ventilation is carried out.

13. The process in accordance with claim 12, wherein the process is carried out with a computer program on the computer.

* * * * *